United States Patent [19]

Bowser et al.

[11] Patent Number: 4,839,161

[45] Date of Patent: Jun. 13, 1989

[54] COSMETIC PRODUCTS

[76] Inventors: Paul A. Bowser, Dorset House, Latchford Road, Gayton, Wirral L60 3RW; Ingrid C. Sturmey, Wirral, both of England

[21] Appl. No.: 89,210

[22] Filed: Aug. 25, 1987

[30] Foreign Application Priority Data

Aug. 29, 1986 [GB] United Kingdom ............... 8620896

[51] Int. Cl.$^4$ .......................... A61K 7/40; A61K 7/42; A61K 7/44

[52] U.S. Cl. ........................................ 424/59; 424/60; 514/546; 514/552; 514/557; 514/558; 514/847; 514/861; 514/863; 514/873; 514/937

[58] Field of Search ................... 424/59, 60; 514/557, 514/546, 552, 558, 861, 863, 847, 873

[56] References Cited

U.S. PATENT DOCUMENTS

| | | | |
|---|---|---|---|
| 3,098,795 | 7/1963 | Kreps | 424/68 |
| 4,234,599 | 11/1980 | Van Scott et al. | 514/557 |
| 4,294,852 | 10/1981 | Wildnauer | 514/557 |
| 4,363,763 | 12/1982 | Peterson | 260/410.7 |
| 4,424,234 | 1/1984 | Alderson et al. | 514/558 |

FOREIGN PATENT DOCUMENTS

| | | | |
|---|---|---|---|
| 0007785 | 2/1980 | European Pat. Off. | 514/557 |
| 86070 | 8/1983 | European Pat. Off. | 514/557 |
| 0086070 | 8/1983 | European Pat. Off. | 514/557 |
| 1952057 | 6/1970 | Fed. Rep. of Germany | 514/546 |
| 1961146 | 6/1970 | Fed. Rep. of Germany | 514/557 |
| 1297928 | 11/1972 | United Kingdom | 514/557 |

*Primary Examiner*—Dale R. Ore
*Attorney, Agent, or Firm*—Melvin H. Kurtz

[57] ABSTRACT

A therapeutic composition for alleviating or preventing sun-induced desquamation comprises as active ingredients a $C_3$ to $C_{30}$ 2-hydroxyalkanoic acid or an ester thereof together with a sunscreen active ingredient in a therapeutically acceptable vehicle. The active ingredients can also be used in the preparation of the composition for the treatment or prevention of this skin condition which can follow exposure to an excessive amount of sunlight.

4 Claims, No Drawings

COSMETIC PRODUCTS

FIELD OF INVENTION

The invention relates to a therapeutic composition and its use in the treatment or prevention of certain skin disorders, and more particularly to the use of an a 2-hydroxyalkanoic acid, or an ester thereof, together with a sunscreen active ingredient, in the preparation of therapeutic compositions for the treament or prevention of a specified skin disorder.

The therapeutic composition is intended for topical application to human skin, particularly to treat and/or to prevent desquamation which can follow excessive exposure of the skin to sunlight. The therapeutic composition can furthermore reduce erythema which can also result from excessive exposure of the human skin to sunlight.

BACKGROUND AND PRIOR ART

When normal human skin is exposed to an excessive amount of sunlight, there is usually an inflammatory response which can result in erythema, often described as sunburn. This can subsequently lead to peeling of the upper layer of the skin which can detract from the appearance of the skin, particularly with loss of tan, and which can lead to dehydration and more serious damage to the skin.

Treatment of the skin with a sunscreen prior to exposure to sunlight can prevent, or at least limit, erythema. However, if erythema is not limited, sunscreens have little or no effect on subsequent skin peeling (desquamation). Conventional treatment of skin following overexposure to sunlight usually involves topical application of a moisturiser such as an oil-in-water cream, but this will generally only provide a cooling effect with some relief of the burning and itching sensation that accompanies erythema. Usually it will not prevent peeling of the skin.

It has been proposed in U.S. Pat. No. 4,424,234 (Lever Brothers Company) to provide a cosmetically acceptable aqueous composition for topical application to human skin to provide skin benefit, the composition comprising an hydroxylated $C_6$–$C_{10}$ carboxylic acid and a cosmetically acceptable vehicle other than water. Among a long list of possible cosmetically acceptable vehicles are sunscreen agents, but there is no suggestion in this reference that the combination of an hydroxylated $C_6$–$C_{10}$ carboxylic acid together with any specified sunscreen agent can be used in the prevention or treatment of sun-induced desquamation.

Applicants have now discovered, contrary to expectation, that topical application of a composition containing both a 2-hydroxyalkanoic acid, or an ester thereof, and a sunscreen active ingredient can be used in the treatment and/or prevention of sun-induced desquamation.

DEFINITION OF THE INVENTION

Accordingly, the invention provides for the use of a 2-hydroxyalkanoic acid, or an ester thereof, having the structure:

where
R is —H, $C_{2-10}$ alkyl or a monoglyceride, diglyceride or triglyceride residue; and
n is 0, or an integer of from 1 to 27,
or mixtures thereof, together with a sunscreen active ingredient, or mixtures thereof, in the preparation of a therapeutic composition for treatment or prevention of sun-induced desquamation.

The inventions also provides a therapeutic composition for alleviating or preventing skin damage characterised by sun-induced desquamation, which composition comprises as active ingredients a therapeutically effective amount of a desquamation inhibitor chosen from 2-hydroxyalkanoic acids and esters thereof, as hereinbefore defined, and a mixture thereof, together with a sunscreen active ingredient, or a mixture thereof, in a therapeutically acceptable vehicle for topical application.

The invention also provides a method for alleviating the symptoms of sun-induced desquamation comprising topically applying to involved areas of the body an effective amount of a composition comprising as active ingredients, a 2-hydroxyalkanoic acid or an ester thereof, as hereinbefore defined, or a mixture thereof, together with a sunscreen active ingredient, or a mixture thereof, in a therapeutically acceptable vehicle for topical application.

The invention also provides for the use of a therapeutic composition comprising as active ingredients a 2-hydroxyalkanoic acid or an ester thereof, as hereinbefore defined, or a mixture thereof, together with a sunscreen active ingredient, or a mixture thereof, in the treatment or prevention of sun-induced desquamation.

DISCLOSURE OF THE INVENTION

It is accordingly an object of the invention to provide a therapeutic composition containing one or more 2-hydroxyalkanoic acids, or esters thereof, and one or more sunscreen agents which when applied topically to the skin of a person suffering from over-exposure to sunlight will arrest or prevent the development of sun-induced desquamation. Also, it is an object of the invention to provide a therapeutic composition, as herein defined, which can be applied topically to the skin prior to exposure to an excessive amount of sunlight so as to prevent the development of sun-induced desquamation.

The 2-hydroxyalkanoic acid and esters thereof

The therapeutic composition of the invention comprises a 2-hydroxyalkanoic acid or an ester thereof having the structure:

where
R is —H, $C_{2-10}$ alkyl or a monoglyceride, diglyceride or triglyceride residue; and
n is 0, or an integer of from 1 to 27.
Examples of 2-hydroxyalkanoic acids include:
2-hydroxypropanoic acid
2-hydroxytetranoic acid
2-hydroxyhexanoic acid
2-hydroxyoctanoic acid
2-hydroxydecanoic acid
2-hydroxydodecanoic acid
2-hydroxytetradecanoic acid
2-hydroxyhexadecanoic acid
2-hydroxyoctadecanoic acid
2-hydroxyoctaeicosanoic acid, and mixtures thereof.

Preferred 2-hydroxyalkanoic acids are 2-hydroxypropanoic, 2-hydroxyhexanoic acid and 2-hydroxyoctanoic acid.

Examples of esters of 2-hydroxyalkanoic acids include:
2-hydroxypropanoic acid ethyl ester
2-hydroxypropanoic acid propyl ester
2-hydroxytetranoic acid ethyl ester
2-hydroxyhexanoic acid methyl ester
2-hydroxyhexanoic acid ethyl ester
2-hydroxyoctanoic acid hexyl ester
2-hydroxyoctanoic acid methyl ester
2-hydroxyoctanoic acid ethyl ester
2-hydroxyoctanoic acid pentyl ester
2-hydroxyoctanoic acid octyl ester
2-hydroxyoctadecanoic acid ethyl ester
2-hydroxyoctanoic acid monoglyceride
2-hydroxyoctanoic acid diglyceride
2-hydroxyoctanoic acid triglyceride, and mixtures thereof.

The amount of 2-hydroxyalkanoic acid or ester thereof to be employed in accordance with the invention, as a therapeutically effective amount, will normally be from 0.1 to 20%, preferably from 0.5 to 10% and most preferably from 0.5 to 2% by weight of the therapeutic composition.

The sunscreen active ingredient

The therapeutic composition of the invention also comprises one or more sunscreen active ingredients.

Examples of sunscreen active ingredients include:
p-Aminobenzoic acid
Ethyl dihydroxypropyl p-aminobenzoic acid (such as Amerscreen P)
Glyceryl p-aminobenzoic acid (such as Escalol 106)
2,4-Dihydroxy benzophenone (such as Uvinul 400)
2-Ethoxyethyl-p-methoxycinnamate (such as Giv Tan F)
Di-ethanolamine p-methoxycinnamate (such as Parsol Hydro)
2-Ethylhexyl salicylate (such as Sun Arome WMO)
Homomenthyl salicylate (such as Filtrosol A)
2-Phenylbenzimidazole-5-sulphonic acid (such as Eusolex 232)
Ethylhexyl p-methoxycinnamate (such as Parsol MCX).
3-(4-Methylbenzylidine) camphor (such as Eusolex 6300)
2-Hydroxy-4-methoxy benzophenone (such as Eusolex 4360)
Butylmethoxydibenzoylmethane (such as Parsol 1789)
4-isopropyl dibenzoylmethane (such as Eusolex 8020)

The amount of the sunscreen active ingredient to be employed in accordance with the invention, as a therapeutically effective amount, will normally be from 0.01 to 10%, preferably from 0.1 to 5% and most preferably from 1 to 5% by weight of the therapeutic composition.

Therapeutically acceptable vehicle

The therapeutic composition of the invention also comprises a therapeutically acceptable vehicle, usually in the form of a lotion, cream, ointment, gel, powder, solid stick or aerosol concentrate formed from cosmetically acceptable ingredients as conventionally employed in the art.

The amount of the therapeutically acceptable vehicle to be employed in accordance with the invention will normally form the balance of the therapeutic composition after taking account of the 2-hydroxyalkanoic acid and/or ester thereof, the sunscreen active ingredient and optional ingredients. Accordingly, the therapeutically acceptable vehicle with normally form from 50 to 99.89%, preferably from 70 to 99.4% by weight of the therapeutic composition.

OPTIONAL INGREDIENTS

The therapeutic composition according to the invention can also optionally contain further ingredients in addition to those which are conventionally used for the provision of the therapeutically acceptable vehicle.

Accordingly, in additon to ingredients conventionally used in preparing a lotion, cream, ointment, gel, powder, solid stick and aerosol concentrate, the therapeutic composition can optionally comprise further ingredients such as a perfume, colourant, preservative, antioxidant, emollient or aerosol propellant.

PREPARATION OF THE THERAPEUTIC COMPOSITION

The therapeutic composition of the invention can be prepared in the form of a solution, lotion, gel, cream, ointment, solid stick, aerosol or powder, or in any other form suited to administration topically to human skin.

When the therapeutic composition is a liquid, such as a lotion or aerosol, or a semi-liquid such as a gel, cream or ointment, or a solid stick, then it is usually necessary to dissolve an effective quantity of the 2-hydroxyalkanoic acid and/or ester thereof and the sunscreen agent in water or ethanol or other aqueous or non-aqueous therapeuticly acceptable vehicle, and then to admix this solution, if desired, in a conventional manner with a suitable cream or ointment base containing, for example an oil or silicone oil and water, or stick base containing a gelling agent such as sodium stearate, or with a normally liquefiable gaseous propellant in order to prepare the therapeutic composition.

When the therapeutic composition is a powder, then it is usually necessary to admix the 2-hydroxyalkanoic acid and/or ester thereof and sunscreen with a powder diluent, such as talc, starch, kaolin, Fuller's earth or other suitable powder base, in order to provide the therapeutic in powder form.

If desired, other therapeuticly acceptable carriers, diluents or emollients can be incorporated in the therapeutic composition according to the invention, in order to facilitate even distribution over the affected area of the skin at a concentration or dosage suitable for treatment or prevention of the sun-induced desquamation.

It is also possible to incorporate in the therapeutic composition according to the invention other therapeutic active substances which may further improve the treatment of skin disorders.

Adjustment of pH

When the therapeutic composition contains water, then the aqueous phase should have a pH value of from 2 to 9, preferably 3 to 6 and ideally from 4 to 5.

Although therapeutic compositions having a pH value of less than 2 are likely to be effective in the treatment or prevention of sun-induced desquamation, topical application of such compositions has been found to produce stinging, burning or irritation. Therapeutic compositions having a pH value of greater than 9 are likely to exhibit reduced effectiveness in the treatment or prevention of sun-induced desquamation.

Any suitable therapeuticly acceptable pH adjustant can be employed to set the pH of the composition at a desired value. Examples of pH adjustants include alkanolamines, especially triethanolamine and buffers such as lactic acid/triethanolamine lactate.

METHOD OF TREATMENT

The invention also provides a method for the treatment or prevention of sun-induced desquamation in man, which method of treatment comprises applying to involved areas of the skin a therapeutically effective amount of a composition comprising from 0.1 to 20% by weight of the 2-hydroxyalkanoic acid and/or ester thereof and from 0.01 to 10% by weight of the sunscreen agent, together with a therapeutically acceptable vehicle.

In general, a therapeutically effective amount of the composition according to the invention which can be applied topically to human skin in order to reduce or prevent the occurence of sun-induced desquamation will be from 0.1 g to 1 g over an area of skin of 100 sq cm. This amount conveniently can be applied once or twice daily, in particular before exposure to sunlight. Higher or lower doses can be applied if desired.

EXAMPLES OF THE INVENTION

The following clinical studies illustrate the treatment of skin disorders with therapeutic compositions according to the invention. In each of the following examples, human subjects were treated by topical application of a formulation containing both 2-hydroxyoctanoic acid and a sunscreen active ingredient. The amounts expressed as percentages are by weight.

Example 1

Three patients who had been subjected to excessive sunlight and had developed erythema on the face were treated in the affected areas by topical application of an oil-in-water cream containing 2-hydroxyoctanoic acid (1%) and a sunscreen (Parsol MCX, 2%). The treatment was repeated night and morning on three consecutive days and the anticipated peeling of the skin to result in desquamation was totally prevented.

Example 2

One person suffering from extensive peeling of the skin (desquamation) following exposure to an excessive amount of sunlight, which had previously resulted in erythema, was treated by topical application of a cream containing 2-hydroxyoctanoic acid (1%) together with a sunscreen (Parsol MCX, 1.5% and Parsol 1789, 0.5%). This treatment was repeated night and morning for one week and further peeling of the skin was prevented.

Example 3

One female subject, whose arms are habitually subject to severe sunburn and desquamation following exposure to sunlight was treated prophilactically by applying to the left arm a composition containing 2-hydroxyoctanoic acid (1%) and a sunscreen (Parsol 1789 1%), and to the other arm a conventional oil-in-water moisturising lotion.

After exposure to sun, it was found that the left arm was completely protected against sun-induced desquamation, whereas the right arm suffered severe skin peeling and associated erythema.

Example 4

One female subject applied to her face a composition comprising 2-hydroxyoctanoic acid (1%) and a sunscreen (Parsol MCX, 3%) before exposure to sunlight. As a result of this treatment no peeling of the skin was observed although this particular subject frequently suffered from sun-induced desquamation.

Example 5

Two female subjects who regularly experience sun-induced desquamation following exposure to excessive amounts of sunlight were treated by topical application of a cream containing 2-hydroxyoctanoic acid (1%) and a sunscreen (Parsol MCX, 1% and Parsol 1785, 1%) before exposure to sunlight. Neither subject suffered sun-induced desquamation.

The above clinical experiments confirm that a mixture of 2-hydroxyoctanoic acid and a sunscreen when applied topically to skin can prevent sun-induced desquamation if applied soon enough. The therapeutic compositions prepared according to the method defined by this invention are accordingly useful prophilactically in preventing the onset of sun-induced desquamation especially if applied topically to skin before exposure to sunlight, and also in the prevention of sun-induced desquamation after exposure to excessive amounts of sunlight and following development of erythema.

The following examples 6 and 7 illustrate therapeutic composition according to the invention. In each case the oil-in-water (o/w) base referred to had the following formulation:

| Ingredient | % w/w |
| --- | --- |
| Mineral oil | 15 |
| Emulsifier | 7 |
| Perfume | 0.7 |
| Preservative | 0.4 |
| Antioxidant | 0.05 |
| Water | to 100 |

Example 6

This example illustrates the formulation of a therapeutic sunburn lotion according to the invention.

| Ingredient | % w/w |
| --- | --- |
| 2-hydroxypropanoic | 5 |
| Parsol MCX | 1.5 |
| Pardol 1789 | 0.5 |
| Perfume | 0.9 |
| in o/w base | to 100 |

Example 7

This example illustrates the formulation of a therapeutic sunburn cream according to the invention.

| Ingredient | % w/w |
| --- | --- |
| 2-hydroxytetranoic acid | 3.5 |
| Eusolex 6300 | 1 |
| Eusolex 8020 | 1.5 |
| Perfume | 1.5 |
| in o/w base | to 100 |

Example 8

This example illustrates the formulation of a therapeutic pre-sun lotion according to the invention. The water-in-oil (w/o) base employed had the following formulation:

| Ingredient | % w/w |
| --- | --- |
| Silicone oil | 20 |
| Emulsifier | 8 |
| Preservative | 0.4 |
| Antioxidant | 0.05 |
| Water | to 100 |
| 2-hydroxypropanoic acid | 4 |
| 2-hydroxyoctanoic acid | 1 |
| Parsol MCX | 3.8 |
| Parsol 1789 | 1 |
| Perfume | 0.5 |
| in w/o base | to 100 |

Example 9

This example illustrate the formulation of a therapeutic pre-sun lotion according to the invention based on the water-in-oil (w/o) base of Example 8.

| Ingredient | % w/w |
| --- | --- |
| 2-hydroxyoctanoic acid ethyl ester | 2 |
| Parsol MCX | 2.5 |
| Parsol 1789 | 0.5 |
| Perfume | 0.8 |
| in w/o base | to 100 |

Example 10

This example illustrates a therapeutic sunburn cream according to the invention based on the water-in-oil (w/o)

| Ingredient | % w/w |
| --- | --- |
| 2-hydroxyoctanoic acid diglyceride ester | 5 |
| Parsol MCX | 2 |
| Parsol 1789 | 1 |
| Perfume | 1 |
| in w/o base | to 100 |

Example 11

This example illustrates a therapeutic sunburn cream according to the invention based on the water-in-oil (w/o) base of Example 8.

| Ingredient | % w/w |
| --- | --- |
| 2-hydroxyoctaeicosanoic acid | 4 |
| Parsol MCX | 2 |
| Parsol 1789 | 1.5 |
| Perfume | 0.5 |
| in w/o base | to 100 |

The topical application of the compositions described in the above examples can be used as pre-sun or post-sunburn treatment for the prevention of alleviation of sun-induced skin peeling and for reducing or eliminating erythema.

What is claimed is:

1. A method of alleviating the symptoms of sun-induced desquamation comprising topically applying to involved areas of the body an effective amount of composition comprising as active ingredients:

(i) a therapeutically effective amount of from 0.1 20% by weight of a desquamation inhibitor selected from group consisting of 2-hydroxyalkanoic acids and esters thereof, having the structure:

$$CH_3(CH_2)_n CH.OH\ COOR$$

where
R is —H, $C_{2-10}$ alkyl or a monoglyceride, diglyceride or triglyceride residue, and
n is 0, or an integer of from 1 to 27, and mixtures thereof; and (ii) a therapeutically effective amount of from 0.01 to 10% by weight of a sunscreen active ingredient or mixtures thereof, in a therapeutically acceptable vehicle for topical application.

2. The composition of claim 1, wherein the desquamation inhibitor is selected from the group consisting of:
2-hydroxypropanoic acid
2-hydroxytetranoic acid
2-hydroxyhexanoic acid
2-hydroxyoctanoic acid
2-hydroxydecanoic acid
2-hydroxydodecanoic acid
2-hydroxytetradecanoic acid
2-hydroxyhexadecanoic acid
2-hydroxyoctadecanoic acid
2-hydroxyoctaeicosanoic acid, and
mixtures thereof.

3. The composition of claim 1, wherein the desquamation inhibitor is selected from the group consisting of:
2-hydroxypropanoic acid ethyl ester
2-hydroxypropanoic acid propyl ester
2-hydroxytetranoic acid ethyl ester
2-hydroxyhexanoic acid methyl ester
2-hydroxyhexanoic acid ethyl ester
2-hydroxyoctanoic acid hexyl ester
2-hydroxyoctanoic acid methyl ester
2-hydroxyoctanoic acid ethyl ester
2-hydroxyoctanoic acid pentyl ester
2-hydroxyoctanoic acid octyl ester
2-hydroxyoctadecanoic acid ethyl ester
2-hydroxyoctanoic acid monoglyceride
2-hydroxyoctanoic acid diglyceride
2-hydroxyoctanoic acid triglyceride, and
mixtures thereof.

4. The composition of claim 1, wherein the sunscreen active ingredient is selected from the group consisting of:
p-Aminobenzoic acid
Ethyl dihydroxypropyl p-aminobenzoic acid
Glyceryl p-aminobenzoic acid
2,4-Dihydroxy benzophenone
2-Ethoxyethyl-p-methoxycinnamate
Di-ethanolamine p-methoxycinnamate
2-Ethylhexyl salicylate
Homomenthyl salicylate
2-Phenylbenzimidazole-5-sulphonic acid
Ethylhexyl p-methoxycinnamate
3-(4-Methylbenzylidine) camphor
2-Hydroxy-4-methoxy benzophenone
Butylmethoxydibenzoylmethane
4-Isopropyl dibenzoylmethane

* * * * *